United States Patent [19]
Jolly

[11] Patent Number: 5,312,756
[45] Date of Patent: May 17, 1994

[54] TOTAL ORGANIC CARBON (TOC) AND TOTAL INORGANIC CARBON (TIC) CALIBRATION SYSTEM

[75] Inventor: Clifford D. Jolly, Lakewood, Colo.

[73] Assignee: Umpqua Research Company, Myrtle Creek, Oreg.

[21] Appl. No.: 998,401

[22] Filed: Dec. 29, 1992

Related U.S. Application Data

[63] Continuation-in-part of Ser. No. 730,122, Jul. 15, 1991, abandoned.

[51] Int. Cl.$^5$ .................... G01N 33/18; G01N 1/00; G01N 30/96
[52] U.S. Cl. .................................. 436/8; 436/19; 436/145; 436/146; 436/174; 436/178; 422/88; 73/23.41
[58] Field of Search ............. 436/146, 8, 19, 145, 436/174, 178; 422/88, 23.41

[56] References Cited

U.S. PATENT DOCUMENTS

| | | | |
|---|---|---|---|
| 3,322,504 | 5/1967 | Capuano | 436/146 |
| 3,607,071 | 9/1971 | Staffin et al. | 436/146 |
| 3,854,881 | 12/1974 | Cohen | 436/146 |
| 4,248,598 | 2/1981 | Blunck | 436/146 |
| 4,293,522 | 10/1981 | Winkler | 436/146 |
| 4,769,217 | 9/1988 | Sienkiewicz et al. | 436/146 |
| 5,106,754 | 4/1992 | Steele et al. | 436/146 |

Primary Examiner—James C. Housel
Assistant Examiner—Rachel Freed
Attorney, Agent, or Firm—Marger Johnson McCollom & Stolowitz

[57] ABSTRACT

There are essentially three aspects to the present invention. In a first aspect, there is provided solid-phase calibration materials for selectively imparting predetermined inorganic or organic carbon levels to a fluid stream by dissolution, comprising solids that are sparingly and selectively soluble in the fluid stream. In a second aspect, the same materials may be used as standards for calibrating an on-line or off-line carbon analyzer at predetermined TIC and TOC levels in a fluid stream. In a third aspect, there is provided a calibration system that utilizes the standards to impart predetermined levels of selected TIC and TOC levels in a fluid sample stream. In one form of the invention, a process is provided for automatically calibrating analytical instrumentation with respect to total organic carbon and total inorganic carbon. In another form of the invention, a process is provided for continuously maintaining the composition of an aqueous effluent stream from a solid phase, flow-through total inorganic carbon and/or total organic carbon calibration standard module at a predetermined standard condition.

20 Claims, 4 Drawing Sheets

MODULE VOLUME: 2.7 cc. CALCIUM CARBONATE
CHALLENGE SOLUTION: DISTILLED WATER
INFLUENT CONDUCTIVITY: 1.3 micomho/cm.
INFLUENT pH: 5.7.
FLOW RATE: 1.0 ml/min.

MODULE VOLUME: 1.0 cc.   4-IODOBENZOIC ACID
CHALLENGE SOLUTION: DISTILLED WATER
INFLUENT TOC: 0.8 mg/l.
INFLUENT CONDUCTIVITY: 1.3 micomho/cm.
INFLUENT pH: 5.5.
FLOW RATE: 1.0 ml/min.

TOTAL ORGANIC CARBON (TOC) AND TOTAL INORGANIC CARBON (TIC) CALIBRATION SYSTEM

BACKGROUND OF THE INVENTION

This is a continuation-in-part of co-pending patent application Ser. No. 07/730,122 filed on Jul. 15, 1991, now abandoned.

On-line Total Carbon analyzers to assess the inorganic and organic carbon characteristics of fluid streams are in common use. Calibration and/or recalibration of such analyzers has typically been accomplished off-line, for example, by injecting solutions of known composition. Such off-line calibration suffers from a number of drawbacks, including lack of automation and, in some cases, accuracy due to sampling errors. Current methods of on-line calibration typically utilize solutions of known composition and generally high strength. Low strength standards are not used because they are not stable. The problem with the use of such high strength solutions for on-line calibration is that due to their high concentration, an unacceptably long period of time is required for the analyzer to regain its sensitivity and thus its measuring or sensing capacity, often referred to as "recovery time". In the case of measurement of low strength sample solutions, this recovery time problem is especially egregious as the recovery time is especially long (often a matter of hours) due to the very large strength differential between the calibrating solution and the solution whose strength is to be determined.

There is therefore a need in the Total Carbon calibration art for simple, reliable, low level calibration standards that may be used both on-line and off-line and that permit quick recovery of an instruments capacity to measure. These needs and others, which will be apparent to those skilled in the art, are met by the present invention, which is summarized and described in detail below.

SUMMARY OF THE INVENTION

There are essentially three aspects to the present invention. In a first aspect, there is provided solid-phase calibration materials for selectively imparting predetermined inorganic and/or organic carbon levels to a fluid stream by dissolution, comprising solids that are sparingly and/or selectively soluble in the fluid stream. In a second aspect, the same materials may be used as standards for calibrating an on-line, or off-line carbon analyzer at predetermined TIC and/or TOC levels in a fluid stream. In a third aspect, there is provided a calibration system that utilizes the standards to impart predetermined levels of selected TIC and TOC levels in a fluid sample stream.

In one form of the invention, a process is provided for automatically calibrating analytical instrumentation with respect to total organic carbon and total inorganic carbon. The process comprises providing an on-line, gravity-independent, flow-through, solid-phase module for calibration of the analytical instrumentation. Then, an aqueous influent stream is introduced into the on-line, gravity-independent, flow-through, solid-phase module for removing existing levels of inorganic and organic carbon. The solid-phase module has certain desired predetermined chemical characteristics which facilitate the effective and/or efficient operation of the automatically calibrating analytical instrumentation. An amount of total organic carbon and total inorganic carbon is then added to the aqueous influent stream to form an aqueous calibration stream. Next, the aqueous calibration stream is introduced into the analytical instrumentation. Finally, the total organic carbon and total inorganic carbon content of the aqueous calibration stream is analyzed thereby calibrating the analytical instrumentation. This analysis is based on the predetermined amount of total organic carbon and total inorganic carbon added by said on-line, gravity-independent, flow-through, solid-phase modules.

In another form of the invention, a process is provided for continuously maintaining the composition of an aqueous effluent stream from a solid phase, flow-through total inorganic carbon and/or total organic carbon calibration standard module at a predetermined standard condition. This process comprises providing an on-line, gravity-independent, flow-through, solid-phase module for treating an aqueous influent stream. Next, the aqueous influent stream is introduced into the on-line, gravity-independent, flow-through, solid phase module. Finally, the aqueous influent stream is treated by combining solid phase, flow-through preconditioning agents and either one of total inorganic carbon and total organic carbon calibration standard materials.

If the desired predetermined chemical characteristic of the solid-phase module is total inorganic carbon content, the solid-phase module of this invention preferably includes at least one compound selected from an alkali, or an alkaline earth, or a transition metal carbonate, and an organic compound. More preferably, the solid-phase module includes a carbonate of Ba, Ca, Cu, Mg, Pb, Sr, Zn and Zr.

If the desired predetermined chemical characteristic of the solid-phase module is total organic carbon content, the solid-phase module preferably contains benzoic acid, 4-iodobenzoic acid, substituted ion exchange resins, or metal oxalates. The preferred metal oxalates are the oxalates of Ba, Ca, Cu, Mg, Pb, Sr, Zn and Zr.

In another form of the invention, when the predetermined chemical characteristic is total organic carbon content, the solid-phase module can also be the acetate form or the formate form of a weak base anion exchange resin.

A system of the subject invention can also be provided for on-line or off-line calibration of a total carbon analyzer. This system comprises the following:

(a) a sensor for sensing the level of carbon of a fluid stream and producing an output representative of the sensed level of said carbon;

(b) means for supplying an influent fluid sample stream at a predetermined volumetric rate;

(c) at least one solid-phase standard means for imparting to said influent fluid sample stream a predetermined level of TIC or TOC;

(d) means selectively operable to establish first and second fluid sample stream flow paths, the first flow path providing said influent fluid sample stream to said influent fluid sample stream to and through said solid-phase standard means to said sensor; and (e) means for calibrating said output representative of the sensed level of said TIC and TOC with respect to said predetermined level of TIC and TOC in said influent fluid sample stream after the same has been directed through said solid-phase standard means.

The above-described system can also include preconditioning means for preconditioning said influent fluid sample stream to remove impurities therefrom. The preconditioning means can comprise either one of an ion exchange resin and activated carbon.

DETAILED DESCRIPTION OF THE INVENTION

Figure 1:
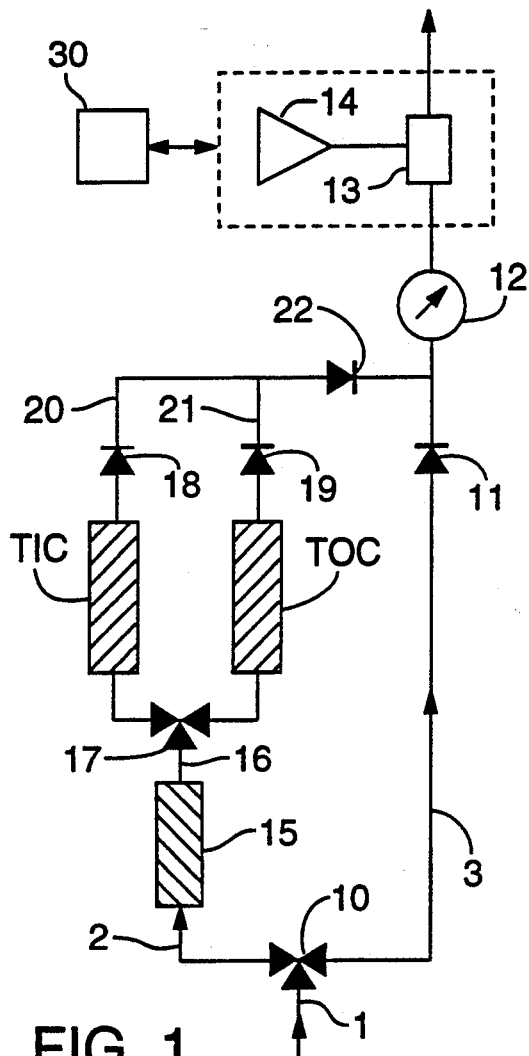
FIG. 1 is a flow schematic showing an exemplary use of the solid-phase standards of the present invention in a system for on-line calibration of a Total Carbon analyzer.

According to the present invention, there is provided a solid-phase standard both for imparting a predetermined chemical characteristic to a fluid stream and for calibrating both on-line and off-line sensors of a given chemical characteristic of a fluid stream. The solid-phase standard is useful in both an on-line and an off-line calibration system for both TIC and TOC analyzers. As mentioned in the Summary above, the solid-phase standards broadly comprise sparingly and selectively soluble solids.

In a preferred application, the chemical characteristics of concern are TIC and TOC, the fluid stream is water, and/or the solids are selected from basic metal carbonates, benzoic acid, halogen-substituted benzoic acids, and substituted ion exchange resins.

In the case of TOC, the solid material is preferably selected from benzoic acid, 4-iodobenzoic acid, and formate and acetate form anion exchange resins, and metal oxalates. In the case of TIC, the solid material may comprise any of the semi-soluble or even relatively insoluble metal carbonates of Ba, Ca, Cu, Mg, Pb, Sr, Zn, and Zr. Especially preferred carbonates for TIC measurement are $BaCO_3$, $CaCO_3$, $CuCO_3$, $PbCO_3$, $SrCO_3$, $ZnCO_3$, $ZrCO_3$, and $PbCO_3$. The solubility of such carbonates may be adjusted by pH adjustment upstream of the standard. This may be accomplished by installing a solid-phase acid bed that produces the desired pH in front of the carbonate TIC calibration. Low pH causes carbonate concentration and thus TIC to increase.

In a closely related aspect of the present invention, there is provided a system for on-line calibration of a carbon analyzer, comprising: the analyzer for sensing the level of the selected carbon form in fluid stream and producing an output representative of the sensed level of the selected carbon form; means for supplying an influent fluid sample stream at a predetermined volumetric rate; at least one solid-phase standard means for imparting to the influent fluid sample stream a predetermined level of the selected carbon form; means selectively operable to establish first and second fluid sample stream flow paths, the first flow path providing the influent fluid sample stream to the analyzer, and the second flow path directing the influent fluid sample stream to and through the solid-phase standard means to said analyzer; and means for calibrating the output representative of the sensed level of the selected carbon content with respect to the predetermined level of the selected carbon content in the influent fluid sample stream after the same has been directed through the solid-phase standard means. In a preferred embodiment of such a system, there is included means for preconditioning the influent fluid stream to adjust the pH to a desired value, or to remove impurities from the stream. The removal of impurities is important so as to allow the solid-phase standard to dictate the strength of the feed solution. In an especially preferred embodiment, the preconditioning means comprises a bed or column of mixed bed ion-exchange resin or activated carbon.

Such a system is exemplified in FIG. 1, where there is shown a schematic of an influent sample or process fluid stream 1 that may flow either through calibration line 2 or sample line 3, normally the latter. When fluid stream 1 flows in sample line 3, it is in fluid communication through diverter valve 10 and check valve 11 with a flow meter 12 (optional) and a Total Carbon analyzer 13. The analyzer 13 generates an output representative of the sensed carbon concentration, and the output is displayed and/or stored on or in a meter 14, the output in turn being monitored either visually or by a microcomputer (not shown). A calibration adjustment system 30 is in feedback and input communication with the sensor 13 and meter 14, indicated by the double-headed arrow and dashed lines. Adjustment of the calibration set point(s) may be by manual adjustment of the meter 14 or by micro-computer for remote calibration. The fluid stream 1 may be diverted, by diverter valve 10, to be in fluid communication with a preconditioning bed 15, such as an ion exchange bed, and activated carbon and then by diverter valve 17, to be in fluid communication with either of two solid-phase calibration standards, designated "TIC" (for Total Inorganic Carbon) and "TOC" (for Total Organic Carbon). A preferred design is a flow-through cartridge containing the solid material of the standard. Fluid flowing through either the TIC or the TOC dissolves the solid-phase standard to a limited extent, imparting a known and precise carbon concentration to the effluent 20 or 21, which can be placed in fluid communication with the flowmeter 12 and/or the analyzer 13 via check valves 18, 19, and 22. It is to be understood that one, two or more of either TIC or TOC's may be used if desired, to provide any number of calibration points.

Figure 2:
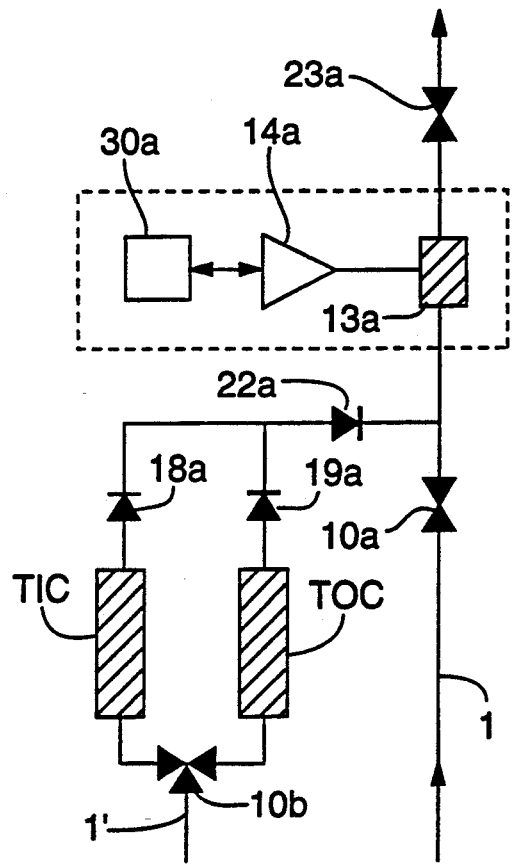
FIG. 2 is another flow schematic of an alternative embodiment of the present invention.

An alternative embodiment of a system incorporating two solid-phase standards of the present invention is illustrated in FIG. 2, wherein like numerals generally designate the same elements as in FIG. 1. An influent sample or process stream 1 flows through valve 10a that is normally open, thence through carbon analyzer 13a. The analyzer 13a generates representative output, which is displayed and/or stored on or in meter 14a, the output being monitored as explained in connection with FIG. 1. Part of the system is a calibration adjustment system 30a, which functions in substantially the same manner shown and described in connection with FIG. 1. When calibration is desired, valves 10a and 23a are closed, valves 10b (normally closed) is opened, and fluid $1^1$ of a known and preferably low TIC and TOC concentration is permitted to flow through either the "TIC" or the "TOC", its flow to the analyzer 13a being controlled by check valves 18a, 19a and 22a.

Figure 3:
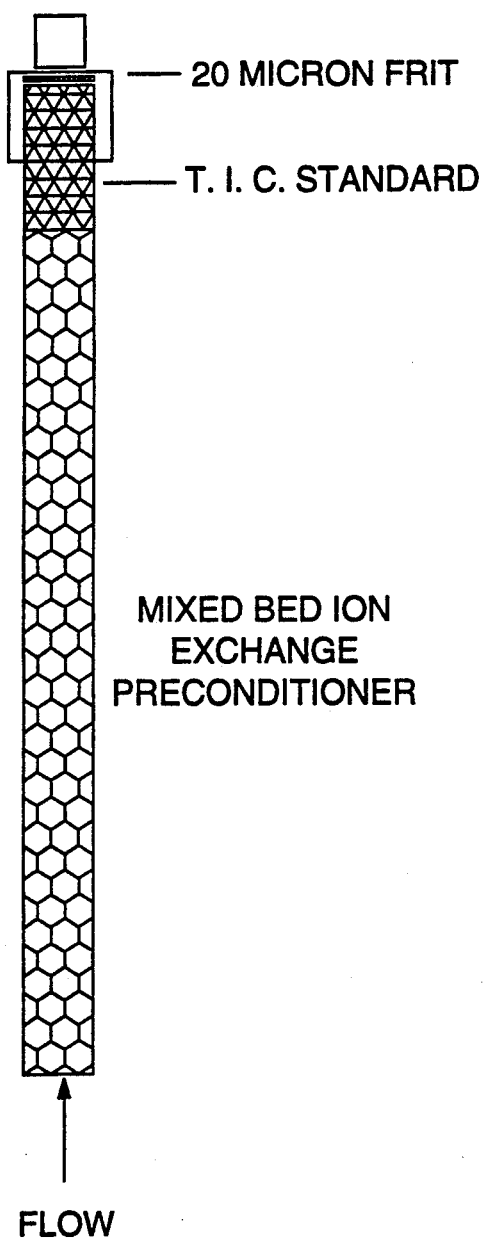
FIG. 3 is a cross-sectional schematic of an exemplary embodiment of the TIC module of the present invention.

FIG. 3 represents an alternative embodiment of the "TIC" of the invention used in FIG. 1 which incorporates a solid preconditioner, such as an ion exchange resin, into the TIC cartridge, upstream of the solid-phase calibration materials.

Figure 4:
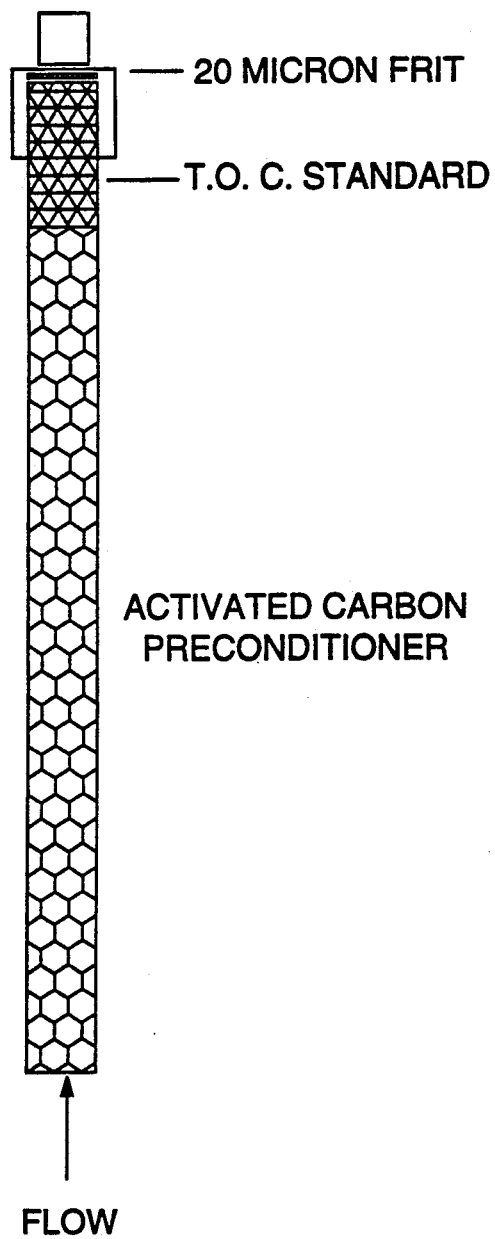
FIG. 4 is a cross-sectional schematic of an exemplary embodiment of the TOC module of the present invention.

FIG. 4 represents an alternative embodiment of the "TOC" solid-phase standard of the invention used in FIG. 1, which incorporates a solid preconditioner 15, such as activated carbon, into the "TOC" cartridge, upstream of the solid-phase calibration material, eliminating the preconditioner 15 in FIG. 1.

In its simplest form, the solid-phase standards of the invention may be prepared by simply packing into a column or cartridge housing 20–100 mesh granules of the solid by itself or with any inert material that is compatible with the intended application, such as porous frits or screens or glass wool.

EXAMPLE 1

Figure 5:
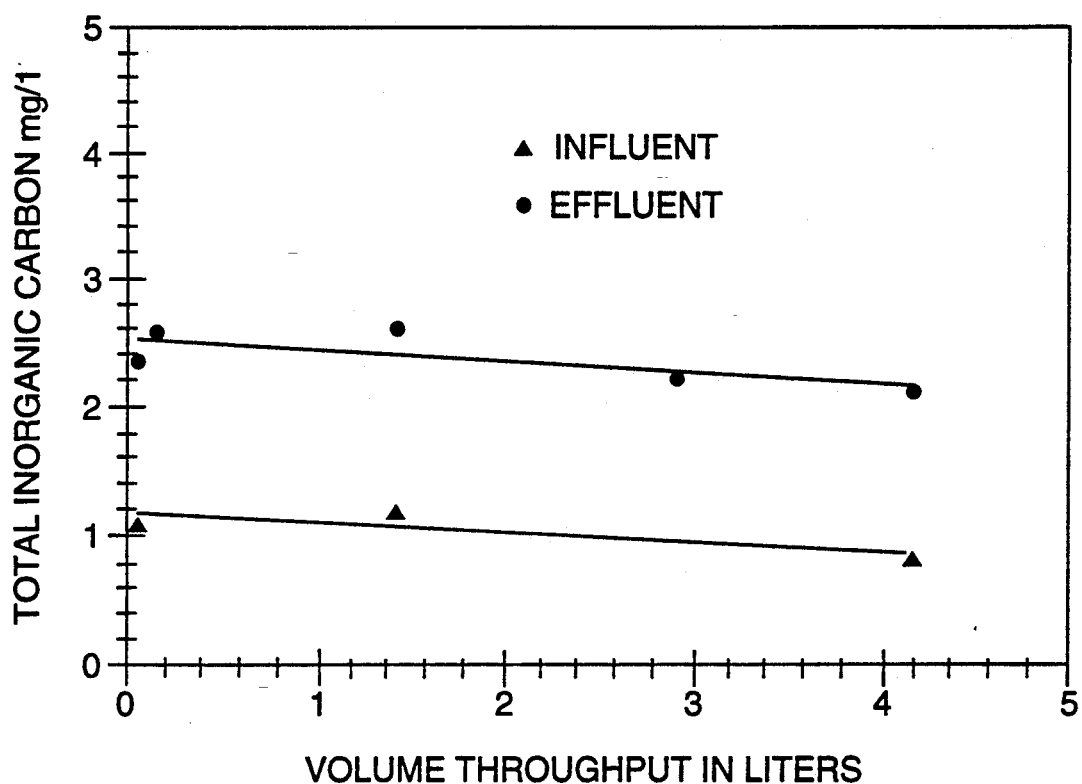
FIG. 5 is a graph showing the TIC addition to distilled water by a TIC module.
Figure 6:
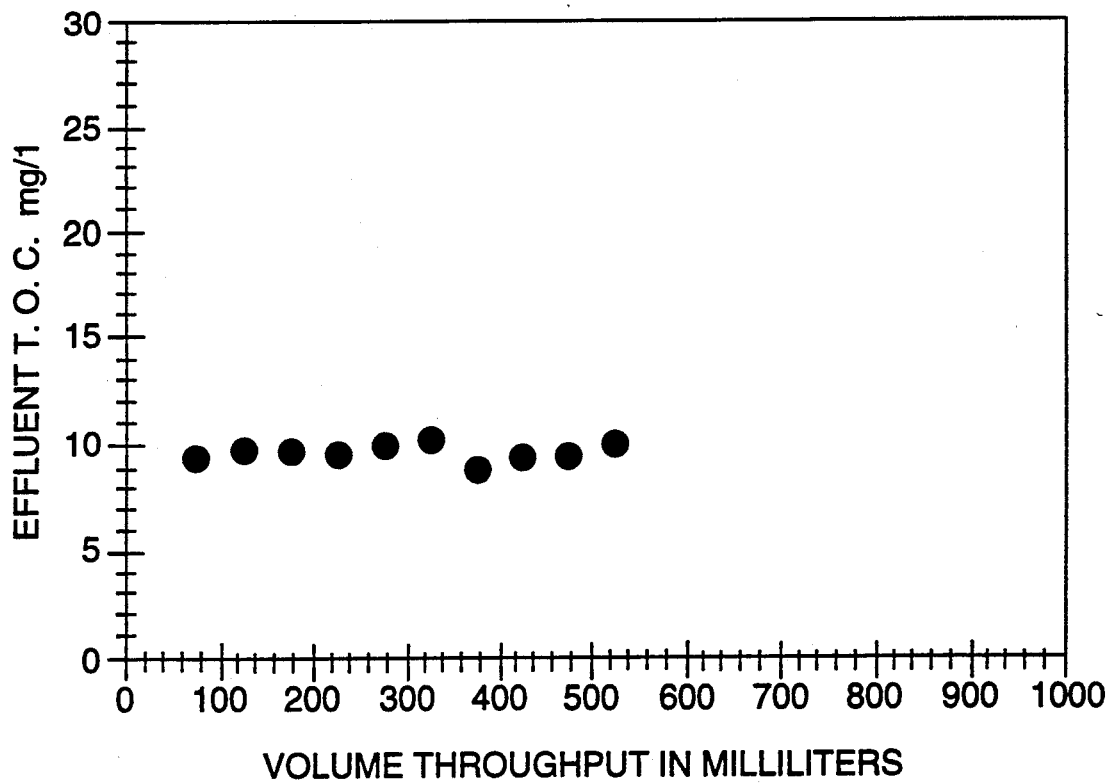
FIG. 6 is a graph showing the TOC addition to distilled water by a TOC module.

The solid-phase calibration standards for calibration of an on-line total carbon analyzer were fabricated and incorporated into an on-line system of substantially the same arrangement shown in FIG. 2. One solid-phase calibration standard, for TIC, comprised granules of $CaCO_3$, 20–100 mesh in a 2.7 cc cylindrical stainless steel flow-through module. The other for TOC, comprised granules of 4-iodobenzoic acid, 100–200 mesh. Process fluid stream 1 comprised of the deionized water. Calibration fluid stream $1^1$ comprised either deionized water or commercially available distilled water having a specific conductance of $\leq 5$ micromho/cm. The system was run continuously with calibration being conducted manually. Flow rates were controlled at 1 ml/min, and calibration was checked against freshly prepared TIC and TOC liquid standards. The results are shown in FIG. 5 for the TIC standard and FIG. 6 for the TOC standard.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

I claim:

1. A process for automatically calibrating analytical instrumentation with respect to either one or both of total organic carbon and total inorganic carbon, which comprises:
   providing on-line, gravity-independent, flow-through, solid-phase modules for calibration of the analytical instrumentation;
   introducing an aqueous influent stream into said on-line, gravity-independent, flow-through, solid-phase modules for removing existing levels of inorganic and organic carbon and adding to the aqueous influent stream a predetermined amount of either one or both of total organic carbon and total inorganic carbon to form an aqueous calibration stream;
   introducing the aqueous calibration stream to said analytical instrumentation, and
   analyzing either one or both of the total organic carbon and total inorganic carbon content of said aqueous calibration stream, and generating an output to said analytical instrumentation based on the predetermined amount of either one or both of total organic carbon and total inorganic carbon added by said on-line, gravity-independent, flow-through, solid-phase modules, thereby calibrating the analytical instrumentation.

2. A process for continuously maintaining the composition of an aqueous effluent stream from a solid phase, flow-through either one or both of Total Inorganic Carbon and Total Organic Carbon calibration standard modules at a predetermined standard condition, which comprises
   providing an on-line, gravity-independent, flow-through, solid-phase module for treating an aqueous influent stream;
   introducing said aqueous influent stream into said on-line, gravity-independent, flow-through, solid phase module; and
   treating said aqueous influent stream by combining therewith solid phase, flow-through preconditioning agents and either one or both of Total Inorganic Carbon and Total Organic Carbon calibration standard materials.

3. The method of claim 1, wherein said on-line, gravity-independent, flow-through, solid-phase module contains at least one compound selected from an alkali, or an alkaline earth, or a transition metal carbonate, and an organic compound.

4. The method of claim 2, wherein said on-line, gravity-independent, flow-through, solid-phase module contain at least one compound selected from an alkali, or an alkaline earth, or a transition metal carbonate, and an organic compound.

5. The method of claim 1, wherein said solid-phase module has a predetermined chemical characteristic which is total inorganic carbon content.

6. The method of claim 2, wherein said solid-phase module has a predetermined chemical characteristic which is total inorganic carbon content.

7. The method of claim 5, wherein said solid-phase module contains an alkali, or an alkaline earth, or a transition metal carbonate.

8. The method of claim 6, wherein said solid-phase module contains an alkali, or an alkaline earth, or a transition metal carbonate.

9. The method of claim 5, wherein said solid-phase module contains a carbonate of Ba, Ca, Cu, Mg, Pb, Sr, Sr, Zn or Zr.

10. The method of claim 6, wherein said solid-phase module contains a carbonate of Ba, Ca, Cu, Mg, Pb, Sr, Sr, Zn or Zr.

11. The method of claim 1, wherein said solid-phase module has a predetermined characteristic which is total organic carbon content.

12. The method of claim 2, wherein said solid-phase module has a predetermined characteristic which is total organic carbon content.

13. The method of claim 11, wherein said solid-phase module contains benzoic acid, 4-iodobenzoic acid, substituted ion exchange resins, or metal oxalates.

14. The method of claim 12, wherein said solid-phase module contains benzoic acid, 4-iodobenzoic acid, substituted ion exchange resins, or metal oxalates.

15. The method from claim 11, wherein said solid-phase module contains the acetate form or the formate form of a weak base anion exchange resin.

16. The method from claim 12, wherein said solid-phase module contains the acetate form or the formate form of a weak base anion exchange resin.

17. A system for calibrating a total carbon analyzer, comprising:

(a) a sensor for sensing the level of carbon of a fluid stream and producing an output representative of the sensed level of said carbon;

(b) means for supplying an influent fluid sample stream at a predetermined volumetric rate;

(c) at least one solid phase standard module for imparting to said influent fluid sample stream a predetermined level of TIC or TOC;

(d) means selectively operable to establish either one of first and second fluid sample stream flow paths, the first flow path providing said influent fluid sample stream through said solid phase standard means to said sensor, the second flow path by-passing the solid phase standard module; and (e) means for calibrating said output representative of the sensed level of said at least one of TIC and TOC with respect to said predetermined level of at least one of TIC and TOC in said influent fluid sample stream after the influent stream has been directed through said solid-phase standard module, including means for generating an output to said analyzer stream based on the predetermined level of either one or both of TIC and TOC.

18. The system of claim 17, including preconditioning means for preconditioning said influent fluid sample stream to remove impurities therefrom.

19. The system of claim 18, wherein said preconditioning means comprises ion exchange resin.

20. A system for calibrating a total carbon analyzer, comprising:

(a) a sensor for sensing a level of carbon of a fluid stream and producing an output representative of the sensed level of said carbon;

(b) means for supplying an influent fluid sample stream at a predetermined volumetric rate;

(c) at least one solid phase standard module for imparting to said influent fluid sample stream a predetermined level of TIC or TOC;

(d) preconditioning means for preconditioning said influent fluid sample stream to remove impurities therefrom, wherein said preconditioning means comprises activated carbon;

(d) means selectively operable to establish either one of first and second fluid sample stream flow paths, the first flow path providing said influent fluid sample stream through said solid phase standard means to said sensor, the second flow path by-passing the solid phase standard module; and (e) means for calibrating said output representative of the sensed level of said TIC and TOC with respect to said predetermined level of TIC and TOC in said influent fluid sample stream after the influent stream has been directed through said solid-phase standard module.

* * * * *